(12) United States Patent
Scott et al.

(10) Patent No.: US 12,156,770 B2
(45) Date of Patent: Dec. 3, 2024

(54) DEPLOYMENT MARKER

(71) Applicant: Boston Scientific Scimed, Inc., Maple Grove, MN (US)

(72) Inventors: Serena Scott, Worcester, MA (US); Rachel M. Williams, Peoria, AZ (US); Thomas DeSimio, Alpine, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/222,712

(22) Filed: Jul. 17, 2023

(65) Prior Publication Data

US 2023/0355348 A1 Nov. 9, 2023

Related U.S. Application Data

(63) Continuation of application No. 17/471,511, filed on Sep. 10, 2021, now Pat. No. 11,744,669, which is a
(Continued)

(51) Int. Cl.
*A61B 90/10* (2016.01)
*A61B 1/018* (2006.01)
(Continued)

(52) U.S. Cl.
CPC ............ *A61B 90/39* (2016.02); *A61B 1/018* (2013.01); *A61M 25/0108* (2013.01);
(Continued)

(58) Field of Classification Search
CPC . A61B 1/018; A61B 2090/3925; A61B 90/39; A61F 2/90; A61F 2/95; A61F 2/9517; A61F 2002/041; A61F 2230/001; A61F 2250/0087; A61F 2250/0096; A61F 2250/0097; A61F 2250/0098; A61M 25/0108

See application file for complete search history.

(56) References Cited

U.S. PATENT DOCUMENTS

| 4,344,436 A | 8/1982 | Kubota |
| 5,749,835 A | 5/1998 | Glantz |
(Continued)

FOREIGN PATENT DOCUMENTS

| CN | 1736346 A | 2/2006 |
| CN | 101370432 A | 2/2009 |
(Continued)

OTHER PUBLICATIONS

International Search Report and Written Opinion dated May 14, 2018 for International application No. PCT/US2018/019668.
(Continued)

*Primary Examiner* — Mark D Remaly
(74) *Attorney, Agent, or Firm* — Seager, Tufte & Wickhem, LLP

(57) ABSTRACT

The present disclosure relates to the field of endoscopy. Specifically, the present disclosure relates to systems and methods which allow the distal portion of a catheter to be visualized within the body using a colored marker and one or more secondary markers. In particular, the present disclosure relates to systems and methods which indicate when a medical device is properly positioned for deployment within a body lumen.

20 Claims, 16 Drawing Sheets

Related U.S. Application Data continuation of application No. 15/904,841, filed on Feb. 26, 2018, now Pat. No. 11,141,238.

(60) Provisional application No. 62/464,202, filed on Feb. 27, 2017.

(51) Int. Cl.
*A61B 90/00* (2016.01)
*A61M 25/01* (2006.01)
*A61F 2/04* (2013.01)
*A61F 2/90* (2013.01)
*A61F 2/95* (2013.01)

(52) U.S. Cl.
CPC . *A61B 2090/3925* (2016.02); *A61F 2002/041* (2013.01); *A61F 2/90* (2013.01); *A61F 2/95* (2013.01); *A61F 2/9517* (2020.05); *A61F 2230/001* (2013.01); *A61F 2250/0087* (2013.01); *A61F 2250/0096* (2013.01); *A61F 2250/0097* (2013.01); *A61F 2250/0098* (2013.01)

(56) References Cited

U.S. PATENT DOCUMENTS

| | | |
|---|---|---|
| 6,068,655 A | 5/2000 | Seguin et al. |
| 2004/0193034 A1 | 9/2004 | Wasicek et al. |
| 2006/0135942 A1 | 6/2006 | Fernandes et al. |
| 2006/0224114 A1 | 10/2006 | Van Sloten et al. |
| 2007/0167822 A1 | 7/2007 | Webler et al. |
| 2008/0183272 A1 | 7/2008 | Wood et al. |
| 2010/0249896 A1 | 9/2010 | Sugimoto et al. |
| 2012/0221093 A1 | 8/2012 | Mchugo |
| 2014/0236064 A1 | 8/2014 | Binmoeller et al. |
| 2016/0158047 A1 | 6/2016 | Treacy et al. |
| 2016/0242943 A1 | 8/2016 | Riedy et al. |

FOREIGN PATENT DOCUMENTS

| | | |
|---|---|---|
| CN | 103347466 A | 10/2013 |
| CN | 103462728 A | 12/2013 |
| CN | 104095696 A | 10/2014 |
| CN | 204274463 U | 4/2015 |
| CN | 105377168 A | 3/2016 |
| JP | 2007500554 A | 1/2007 |
| WO | 9746174 A1 | 12/1997 |
| WO | 2005011788 A1 | 2/2005 |
| WO | 2008091409 A1 | 7/2008 |
| WO | 2009114340 A2 | 9/2009 |
| WO | 2013133081 A1 | 9/2013 |
| WO | 2013173045 A1 | 11/2013 |
| WO | 2015167997 A1 | 11/2015 |

OTHER PUBLICATIONS

Binmoeller et al., "A Novel Lumen-Opposing Stent for Transluminal Drainage of Nonadherent Extraintestinal Fluid," Endoscopy, vol. 43, No. 4, pp. 337-342. Published Online Jan. 24, 2011.

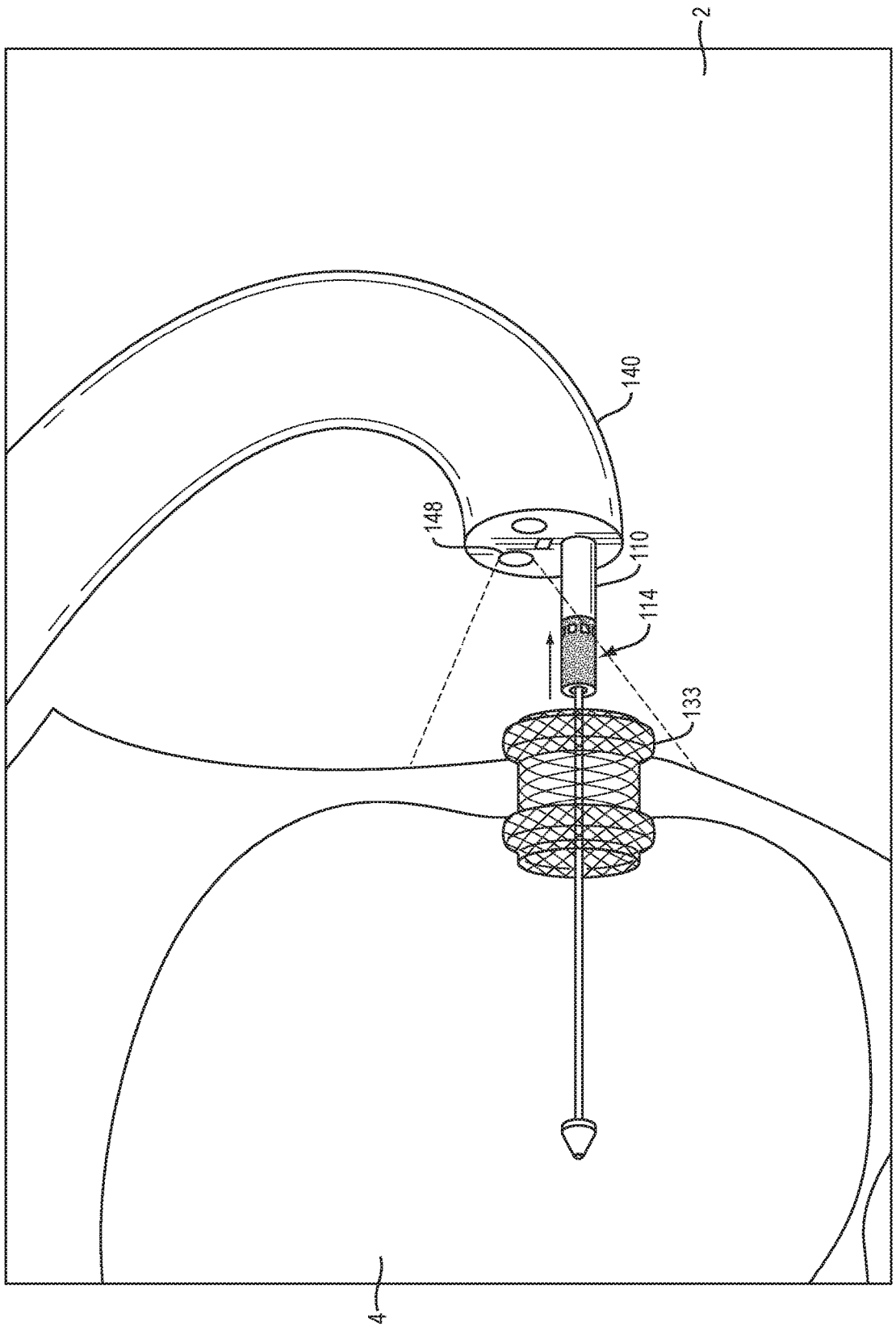

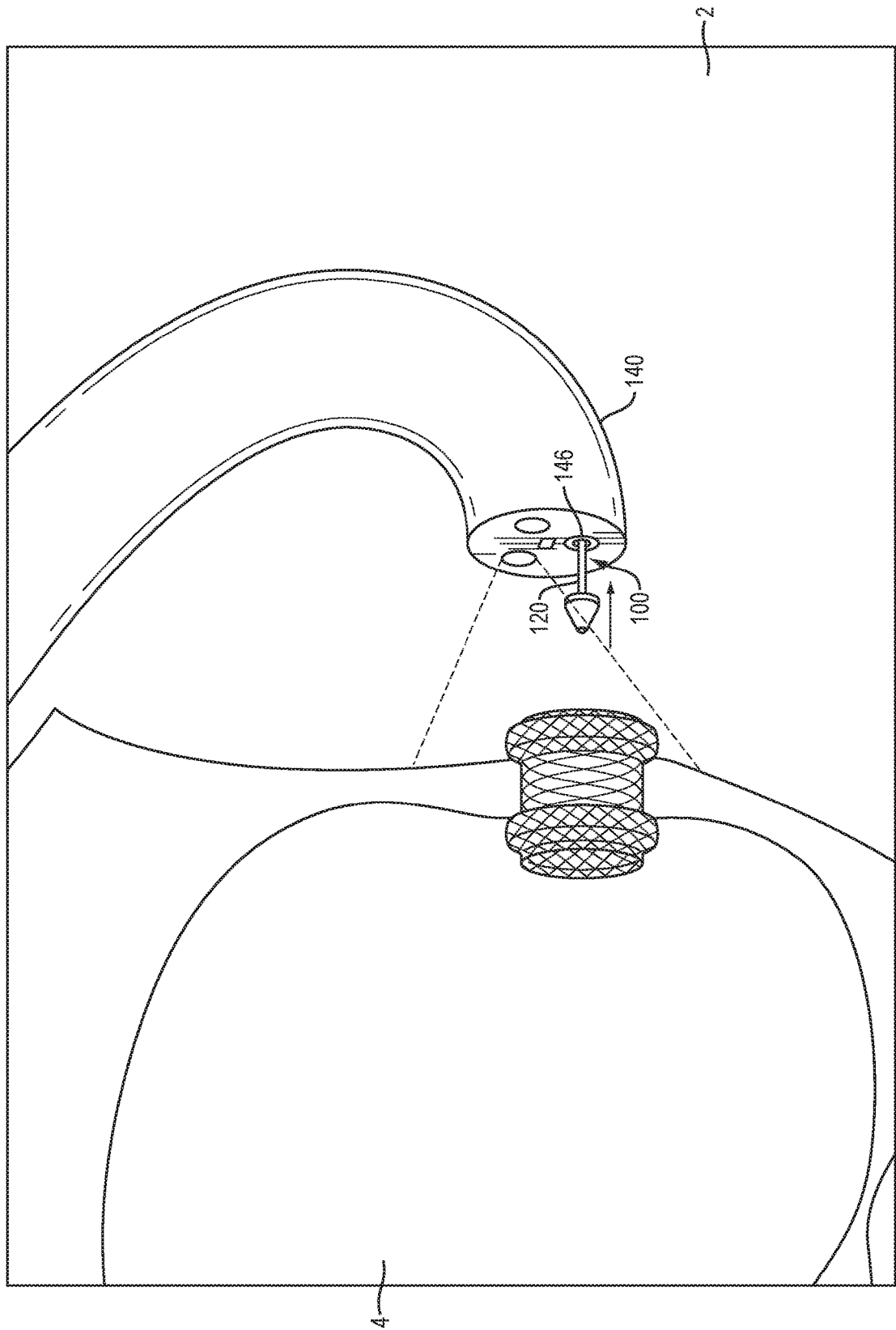

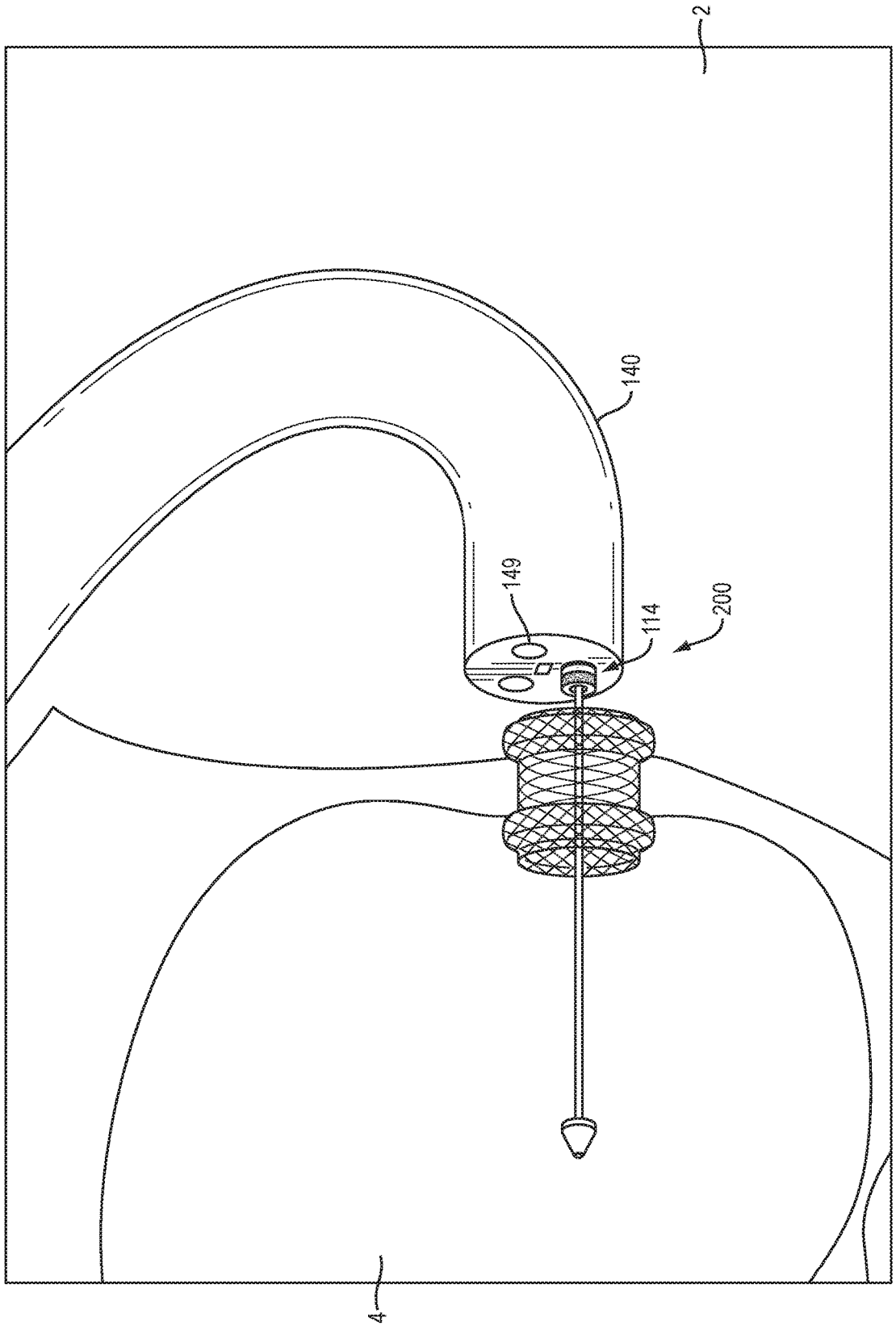

DEPLOYMENT MARKER

CROSS REFERENCE TO RELATED APPLICATIONS

This application is a continuation of U.S. patent application Ser. No. 17/471,511, filed Sep. 10, 2021, which is a continuation of U.S. patent application Ser. No. 15/904,841, filed Feb. 26, 2018, which claims the benefit of priority under 35 U.S.C. § 119 to U.S. Provisional Patent Application Ser. No. 62/464,202, filed on Feb. 27, 2017, the disclosures of which are herein incorporated herein by reference in their entirety for all purposes.

FIELD

The present disclosure relates to the field of endoscopy. Specifically, the present disclosure relates to systems and methods that allow the distal portion of a catheter to be visualized within the body using a colored marker and one or more secondary markers.

BACKGROUND

Medical devices, such as stents, are regularly used to create and/or maintain a conduit between adjacent body lumens or cavities. For example, a drainage stent may be used to drain the contents of a pancreatic pseudocyst, gall bladder or bile duct into the stomach or duodenum. Placement of a drainage stent with ultrasound within the body generally includes a two-step procedure in which a catheter carrying the stent is inserted under ultrasound guidance through the wall of a first body lumen (e.g., gastrointestinal tract) into an adjacent lumen (e.g., pseudocyst) and a distal retention member deployed. The catheter is then retracted and a proximal retention member is deployed within the GI tract. A medical professional may determine that the catheter has been sufficiently retracted by switching to an endoscopic viewing mode, which allows for direct visualization of the catheter and GI tract wall. For example, the appearance of a colored marker on a distal portion of the catheter within the first body lumen may indicate that the catheter has been sufficiently retracted to allow proper deployment of the proximal retention member within the GI tract. For example, the appearance of a colored marker on a distal portion of the catheter within the first body lumen may indicate that the catheter has been sufficiently retracted to allow proper deployment of the proximal retention member within the GI tract.

Unfortunately, a variety of circumstances may cause the proximal retention member to be deployed within the wrong anatomical location. The medical professional may incorrectly determine the stent's position using the ultrasonic viewing mode, forget to switch to the endoscopic viewing mode, accidentally or prematurely release the proximal retention member, and/or have difficulty visualizing the colored marker due to the flow of viscous, cloudy or opaque fluids (e.g., bile, etc.) through the drainage stent. An improperly deployed drainage stent may be difficult to retrieve, e.g., from within the pseudocyst or the body cavity outside of the GI tract, and/or will require a subsequent stent to be placed, extending the procedure, requiring a second procedure, and expending additional time, effort, and cost, with perhaps additional risk to the patient.

Accordingly, various advantages may be realized by delivery systems and methods that allow the distal portion of a catheter to be visualized using a colored marker and one or more secondary markers to indicate the position of a medical device within a patient.

SUMMARY

The present disclosure, in its various aspects, provides advantages in the medical field, such as the field of endoscopy, for systems and methods which allow the distal portion of a catheter to be visualized within the body to indicate when a medical device is positioned for proper deployment.

In one aspect, the present disclosure relates to a system comprising a catheter that includes a proximal end, a distal end, and a lumen extending therebetween. A distal portion of the catheter may include a primary marker and at least one secondary marker. The at least one secondary marker may be disposed within the primary marker. The at least one secondary marker may be disposed on or within a distal portion of the catheter which corresponds to an approximate midpoint of a medical device when loaded on the catheter. The at least one secondary marker may be disposed on or within a distal portion of the catheter which corresponds to an approximate distal end of a medical device when loaded onto the catheter. The at least one secondary marker may include a plurality of secondary markers disposed about a circumference of the catheter. The primary marker may include a colored marker. The at least one secondary marker may include an echogenic material. The at least one secondary marker may include a light sensor.

In another aspect, the present disclosure relates to a system comprising a catheter that includes a proximal end, a distal end, and a lumen extending therebetween. A distal portion of the catheter may include a primary marker and at least one secondary marker. An inner catheter may be slidably disposed within the catheter lumen, and a medical device may be disposed over a distal portion of the inner catheter. The at least one secondary marker may be disposed within the primary marker. The at least one secondary marker may be disposed on or within a distal portion of the catheter which corresponds to an approximate midpoint of the medical device. The at least one secondary marker may be disposed on or within a distal portion of the catheter which corresponds to an approximate distal end of the medical device. The at least one secondary marker may include a plurality of secondary markers disposed about a circumference of the catheter. The primary marker may include a colored marker. The at least one secondary marker may include a light sensor. The at least one secondary marker may include an echogenic material. The medical device may include a self-expanding stent configured to move between a first configuration when disposed within the catheter lumen, and a second expanded configuration when not disposed within the catheter lumen. The system may further include a handle attached to the proximal end of the catheter and a proximal end of the inner catheter, wherein the handle may include a first lock configured to releasably engage the inner catheter, and a second lock configured to releasably engage the catheter. The catheter may move proximally with respect to the inner catheter when the first lock is engaged and the second lock is disengaged. The catheter and inner catheter may be immobilized with respect to each other when the first and second locks are engaged.

In another aspect, the present disclosure relates to a method, comprising advancing a delivery system through a body passage to a first luminal body, wherein the delivery system may include a catheter comprising a distal portion including a primary marker and at least one secondary marker, and a medical device disposed within the catheter. The method may further include imaging a second body adjacent to the first luminal body using ultrasound, advancing the catheter through the wall of the first luminal body into the second body, deploying a distal retention member of the medical device within the second body, proximally retracting the delivery system such that at least a portion of the colored marker on the distal portion of the catheter is disposed within the first luminal body and deploying a proximal retention member of the medical device within the first luminal body. The method may further include, prior to deploying the distal retention member, imaging the at least one secondary marker within the second body. The method may further include, prior to deploying the proximal retention member, imaging the at least one secondary marker within the first luminal body.

BRIEF DESCRIPTION OF THE DRAWINGS

Non-limiting examples of the present disclosure are described with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures:

FIGS. 5A-5H illustrate the steps involved in deploying a stent with a stent delivery system, according to one embodiment of the present disclosure.

FIGS. 6A-6D illustrate the steps involved in deploying a stent with a stent delivery system, according to one embodiment of the present disclosure.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to the deployment of a drainage stent between adjacent body lumens, the systems and methods disclosed herein may be used to position a variety of medical devices, including, but not limited to stents, within a variety of anatomical locations.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from a medical professional when introducing a device into a patient, while the term "proximal" refers to the end closest to the medical professional when introducing a device into a patient.

The present disclosure generally provides a delivery system and method that allows the distal portion of a catheter to be visualized using a colored marker and one or more secondary markers to indicate the position of a medical device within a patient.

Figure 1:
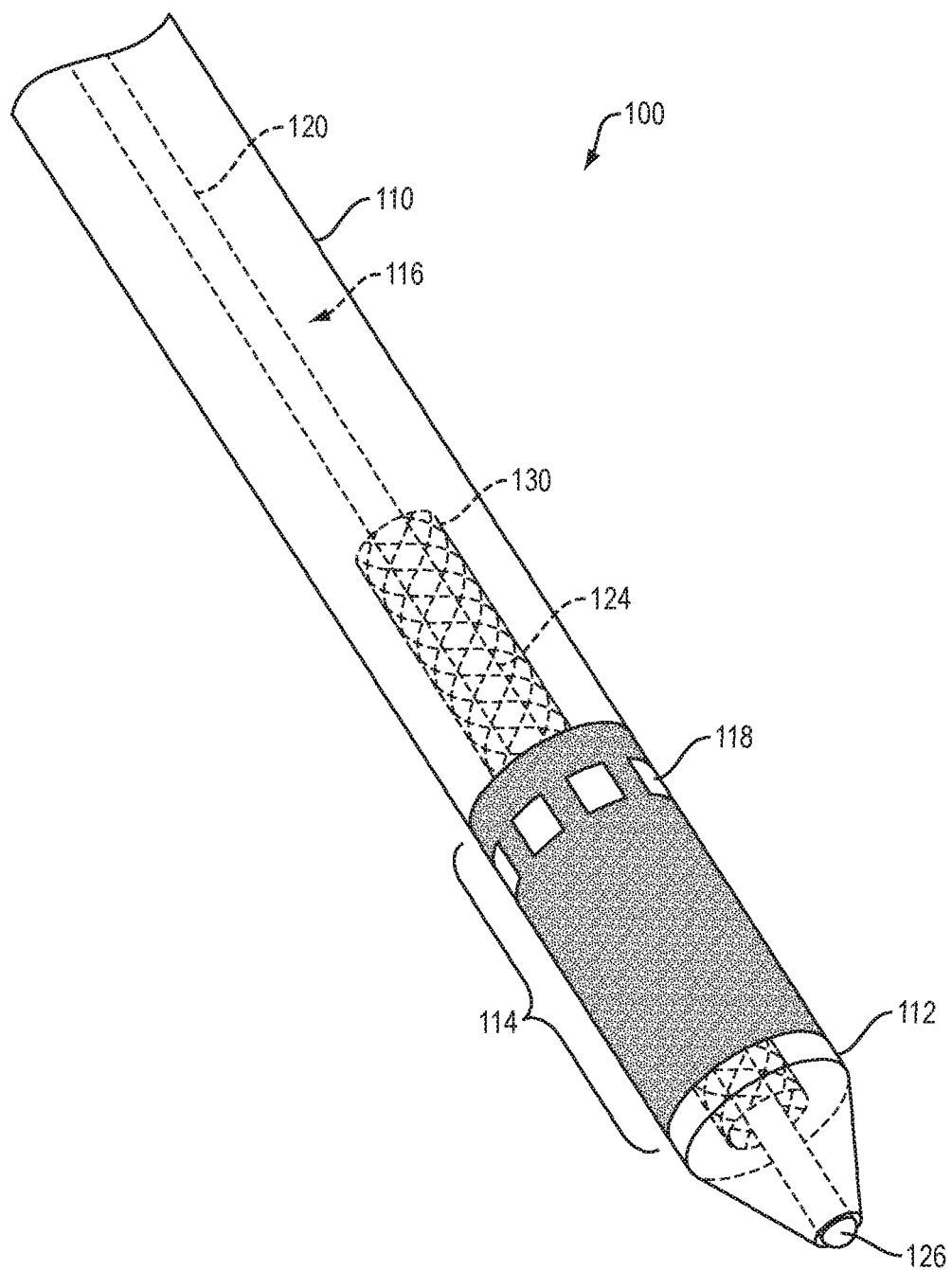
FIG. 1 provides a schematic view of a stent delivery system, according to one embodiment of the present disclosure.

Referring to FIG. 1, in one embodiment, the present disclosure provides a delivery system 100 comprising a catheter 110 that includes a proximal end (not shown), a distal end 112 and a lumen 116 extending therebetween. A distal portion 114 of the catheter 110 may include a primary marker, e.g., a colored region, that is different than the color of the remaining portion of the catheter. By way of non-limiting example, the distal portion 114 of the catheter 110 may include a dark color (e.g., black, etc.) and the remaining portion of the catheter may include a light color (e.g., white, etc.) which contrasts with the dark color when illuminated by a light source. The primary marker may extend a variety of distances along the distal portion 114 of the catheter (e.g., approximately 10 mm or more; approximately 20 mm or more; approximately 30 mm or more) depending on the anatomical location and/or body wall thickness of the target body lumen(s). The catheter 110 may further include at least one secondary marker 118 disposed on or within the distal portion 114, either as part of or separate from the primary marker on the distal portion. For example, a plurality of secondary markers 118 may be disposed (evenly or unevenly) about a circumference of the distal portion. The plurality of secondary markers 118 may be embedded within, affixed to, or integrally formed within an outer surface of the distal portion 114 using injection molding and/or suitable adhesive glues, resins or epoxies as are known in the art. The arrangement of secondary markers 118 about the distal portion 114 of the catheter 110 is not limited to the embodiment depicted in FIG. 1, but may include more or fewer secondary markers arranged in a variety of different shapes, positions, configurations and/or orientations. For example, a plurality of secondary markers may be disposed about the circumference and/or length of the catheter in one or more evenly or unevenly spaced rows or bands. In one embodiment, the at least one secondary marker may include a light sensor (e.g., photodiode, etc.) configured to transmit a signal to an external receiver.

Still referring to FIG. 1, the delivery system 100 may further include an inner catheter 120 within the lumen 116, and slidably disposed with regard to the catheter 110. A medical device 130 may be disposed over a distal portion 124 of the inner catheter 120 within the lumen 116. In one embodiment, the medical device 130 is a stent configured to move between a first (e.g., collapsed) configuration when disposed (e.g., constrained) within the lumen 116 of the catheter 110 and a second (e.g., expanded) configuration when not disposed with the lumen 116. The distal end 112 of the inner catheter 120 may further include a tissue cutting surface 126 (e.g., sharpened surface, electrocautery surface, etc.) for penetrating the wall(s) of a first luminal body and second body.

Figure 2:
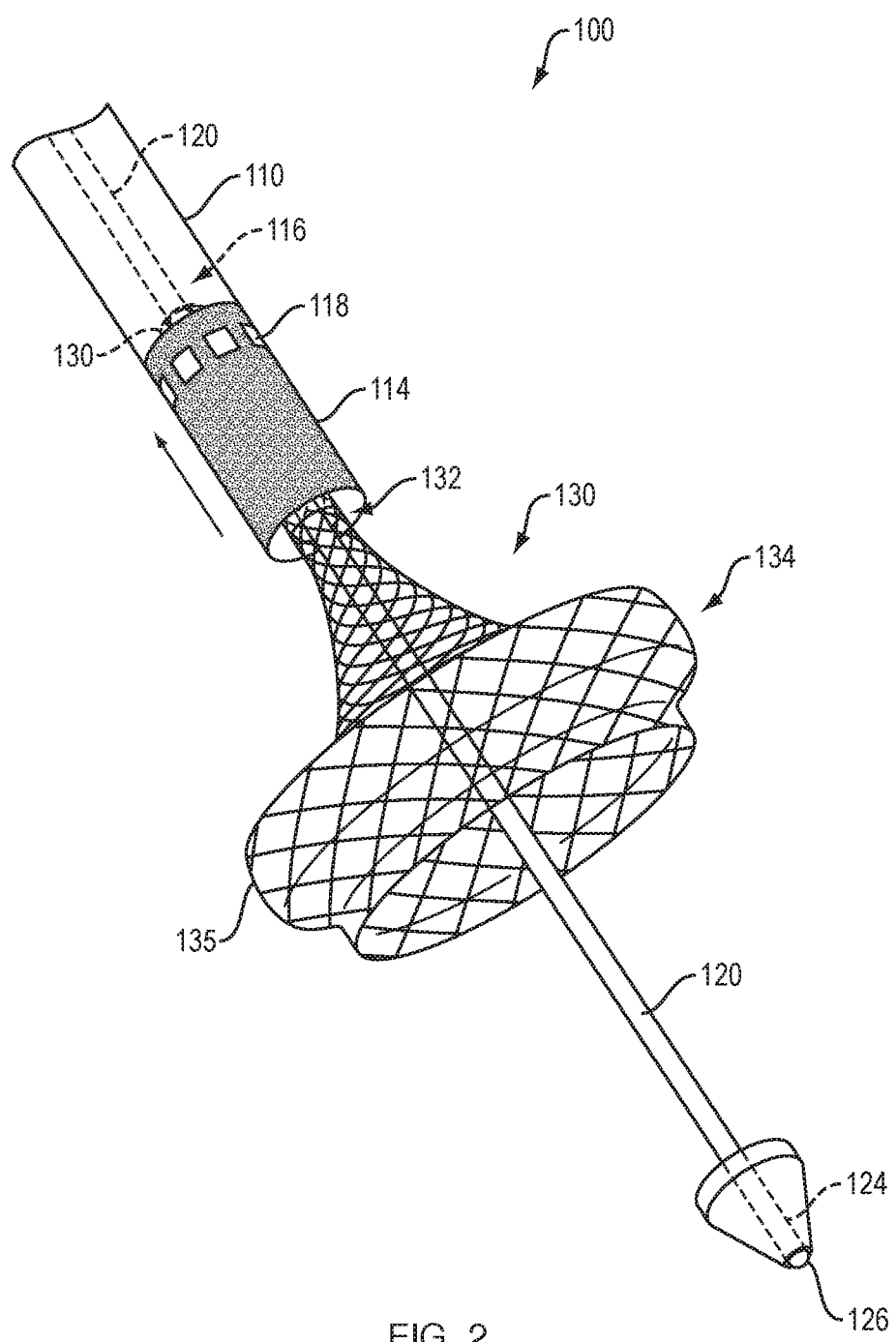
FIG. 2 provides a schematic view of a stent partially deployed from a stent delivery system, according to one embodiment of the present disclosure.
Figure 3:
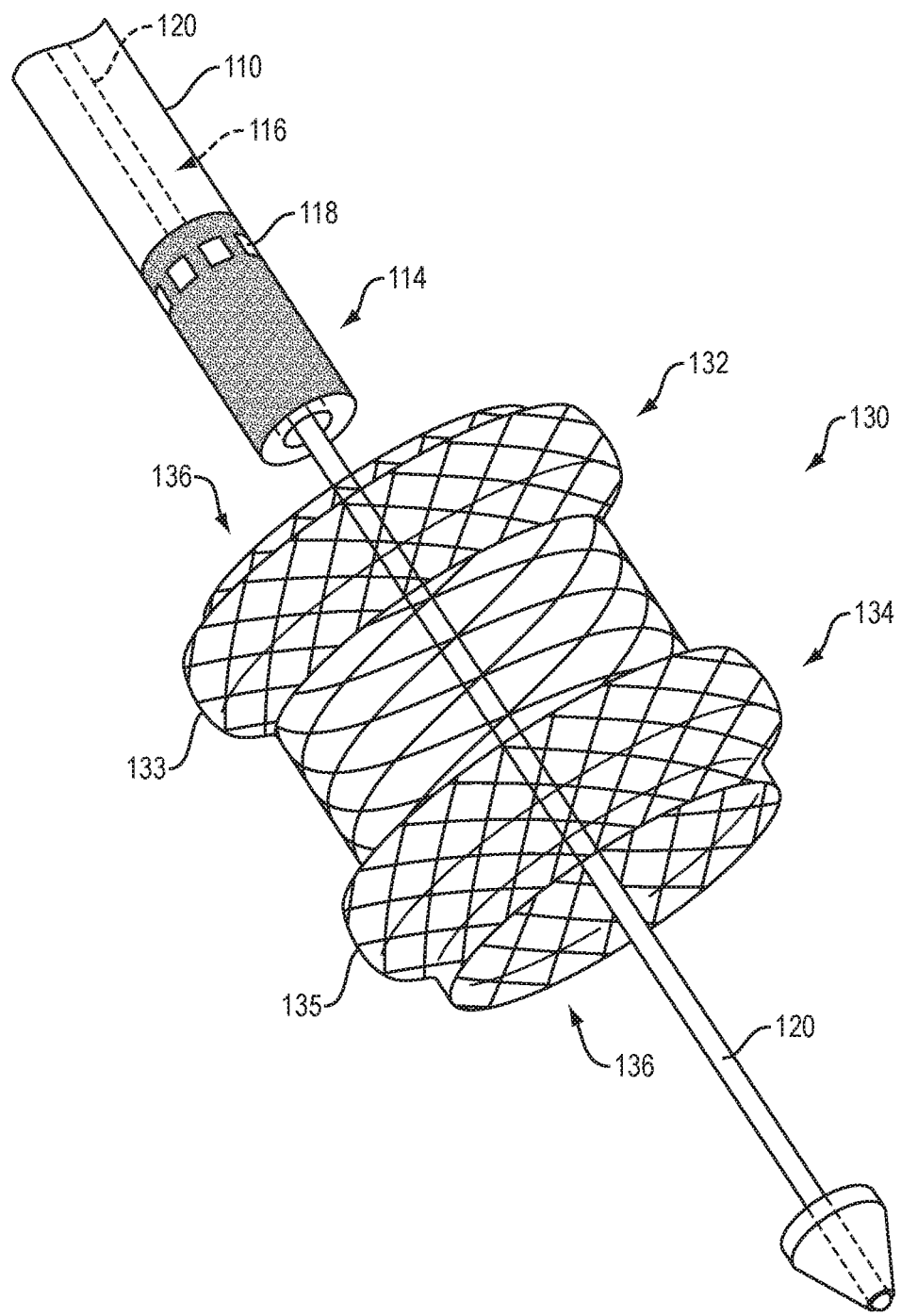
FIG. 3 provides a schematic view of a stent fully deployed from a stent delivery system, according to one embodiment of the present disclosure.

The delivery system 100 may further include a handle (not shown) connected to the respective proximal ends (not shown) of catheter 110 and inner catheter 120. A handle may include a first lock configured to secure the inner catheter 120, and a second lock configured to secure the catheter 110 along/over the inner catheter 120. With the first and second locks engaged, the catheter 110 may be inserted through an endoscope working channel, and the handle may be secured to the proximal portion of the endoscope such that neither the inner catheter 120 nor catheter 110 are able to move. Disengagement of the first lock, but not the second lock, allows the inner catheter 120 and catheter 110 to move together within and through the endoscope working channel (FIGS. 2-3). Disengagement of the second lock, but not the first lock, allows the catheter 110 to be proximally retracted along/over the immobilized (e.g., locked) inner catheter 120 to sequentially release the distal and proximal portions 134, 132 of the stent 130.

In one embodiment, the at least one secondary marker 118 may include a light sensor configured to transmit a signal wirelessly, or via embedded circuitry running along the length of the catheter, to an external receiver. Upon receiving an appropriate signal from the one or more secondary markers 118, the external receiver may cause the second lock (but not the first lock) to disengage. Referring to FIG. 2, as an example, with the second lock (but not the first lock) disengaged, the catheter 110 may be retracted proximally along/over the inner catheter 120 such that the distal portion 134 of the stent exits (e.g., is unconstrained) the lumen 116 of the catheter 110 to form a distal retention member 135. Referring to FIG. 3, the catheter 110 may be further retracted proximally such that the proximal portion 132 of the stent exits the lumen 116 of the catheter 110 to form a proximal retention member 133.

Without limiting stents of the systems of the present disclosure to any specific configuration or design, in one embodiment the stent may be self-expanding such that a distal portion 134 of the stent radially expands to form a distal retention member 135 in the second configuration, and a proximal portion 132 of the stent radially expands to form a proximal retention member 133 in the second configuration. A length of the stent between the distal and proximal portions 134, 132 may decrease in the second configuration, thereby presenting an anchor interface with the retention members to appose a first luminal body and a second body therebetween. A diameter of the stent between the distal and proximal portions 134, 132 may increase in the second configuration (less than the diameter of the distal and proximal retention members 134, 132) to define a lumen 136 which provides a flow path for fluids and material between the apposed walls of the second body and first luminal body.

Figure 4:
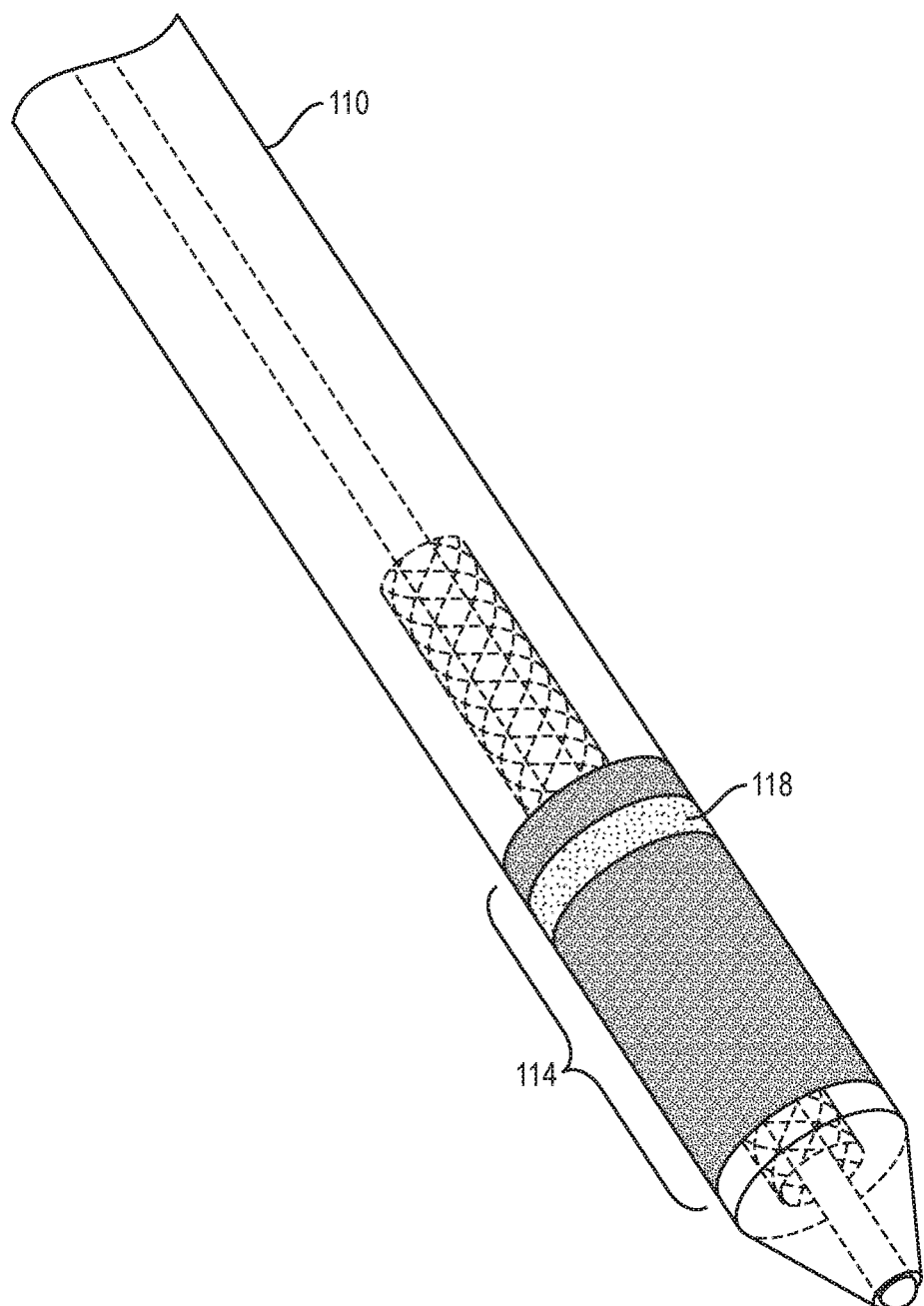
FIG. 4 provides a schematic view of a stent delivery system, according to another embodiment of the present disclosure.

Referring to FIG. 4, in one embodiment, the at least one secondary marker 118 may include an echogenic (e.g., hyperechoic) material disposed in one or more bands about a circumference of the distal portion 114 of the catheter 110. The echogenic material may include a variety of reflective material (e.g., metals, metallic powders, etc.) and/or patterns (e.g., etching, dimples, cross-hatching, etc.) which reflect or "echo" ultrasound waves emitted from an ultrasound transducer, as are known in the art. Although the delivery systems of FIGS. 1 and 4 depict secondary markers 118 that include either light sensor(s) or echogenic marker(s), respectively, in various embodiments the distal portion 114 of the catheter 110 may include both light sensor(s) and echogenic marker (s) arranged in various patterns, positions, orientations and/or configurations, along with the primary marker, e.g., colored marker.

Figure 5A:
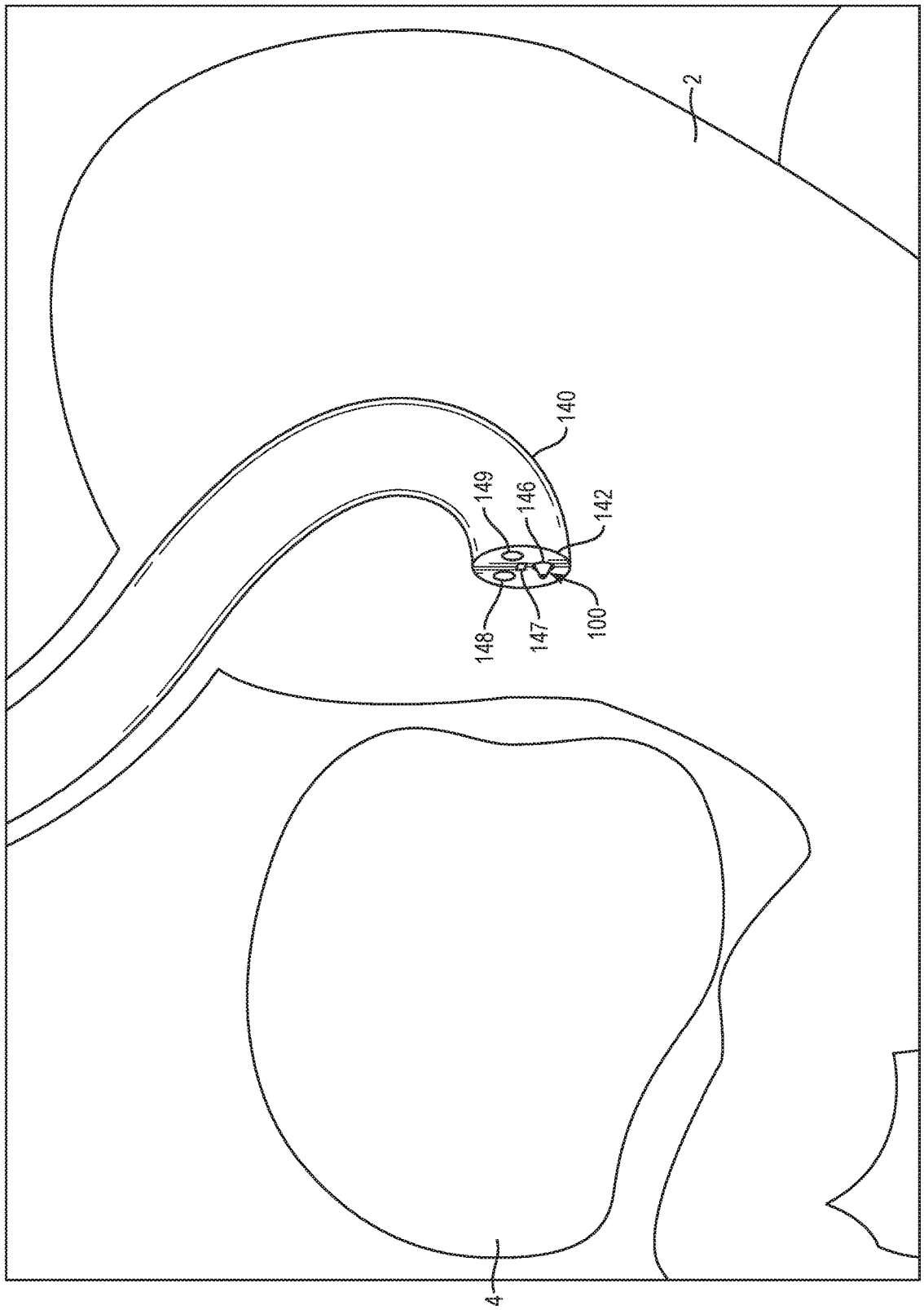
Figure 5B:
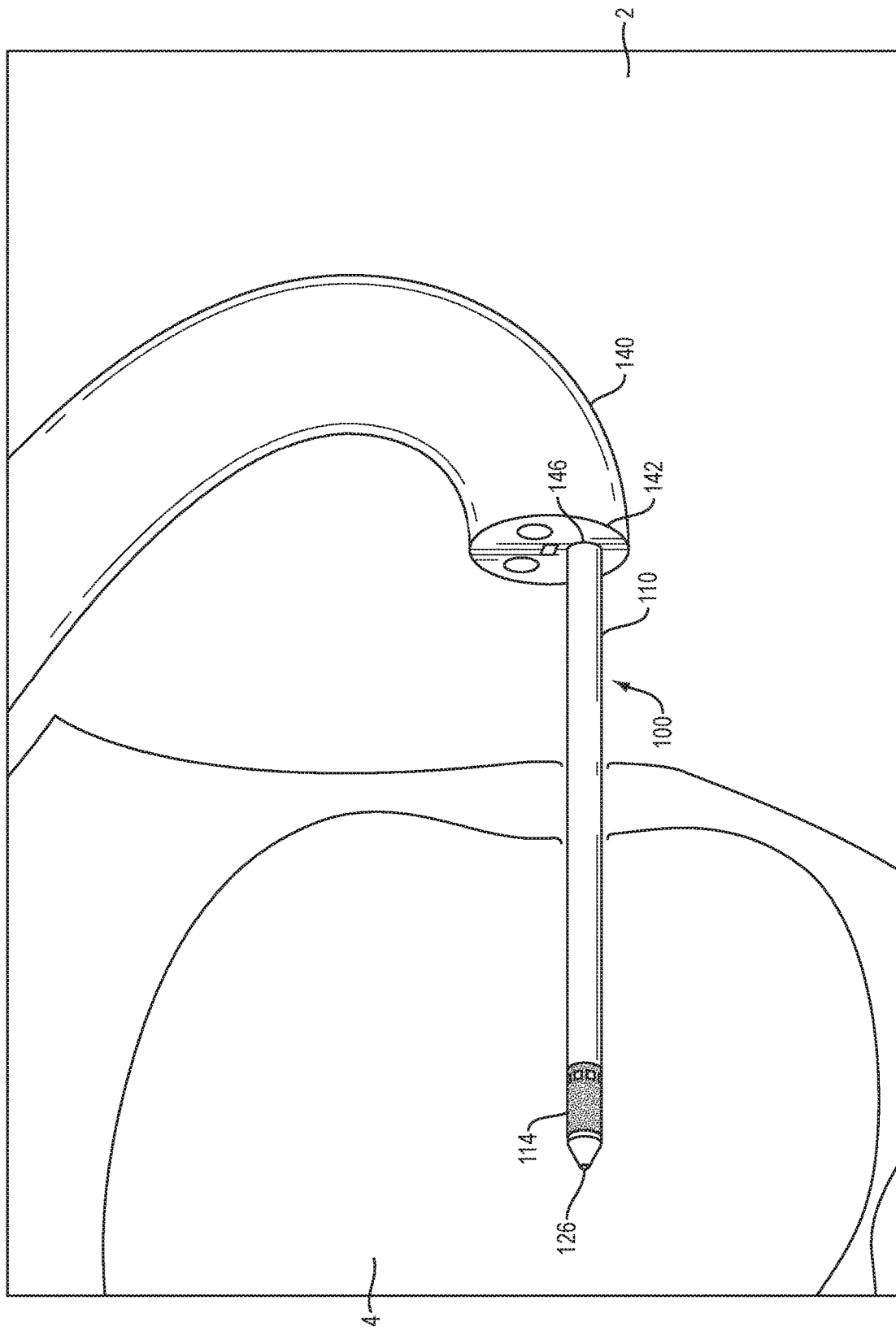
Figure 5C:
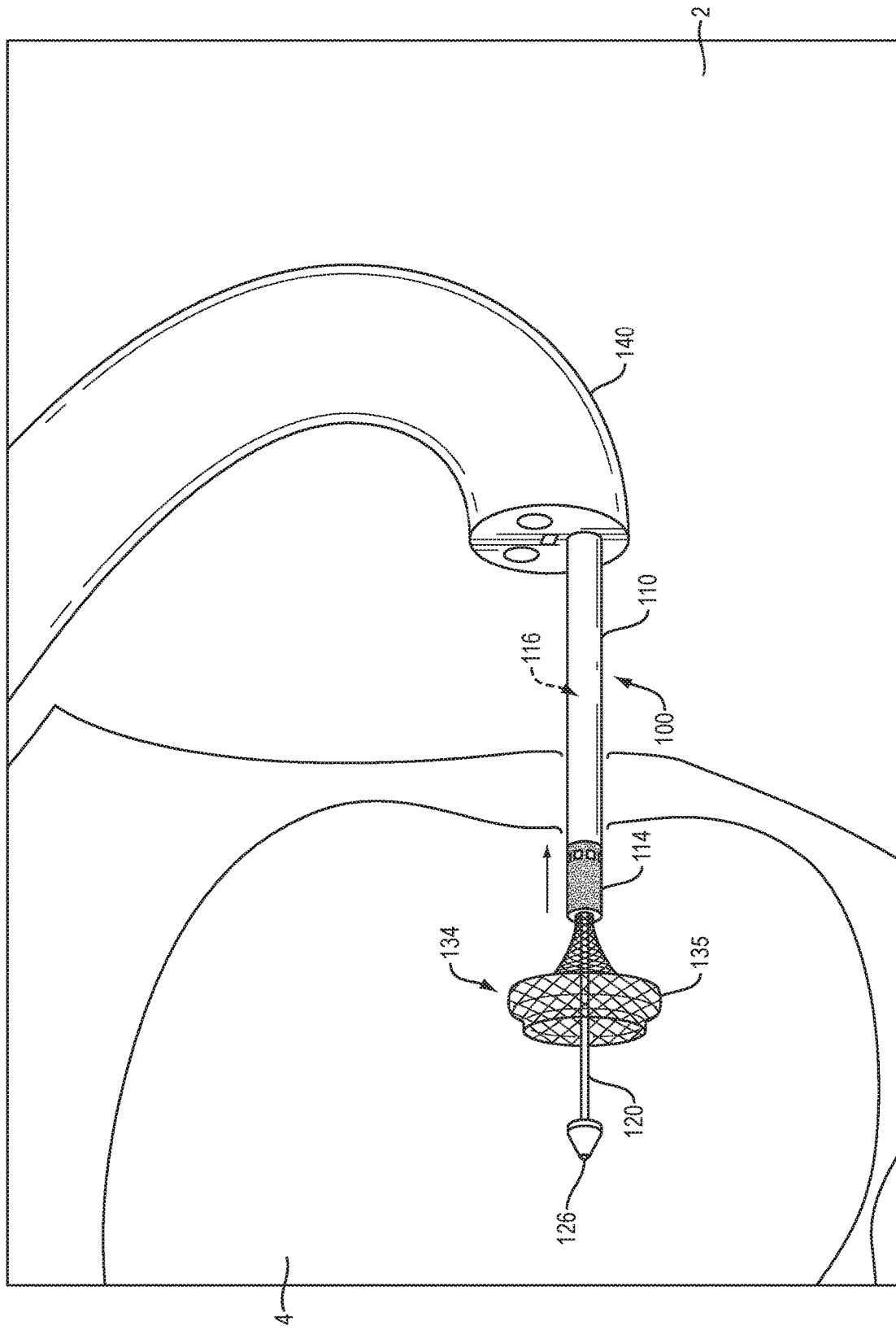
Figure 5D:
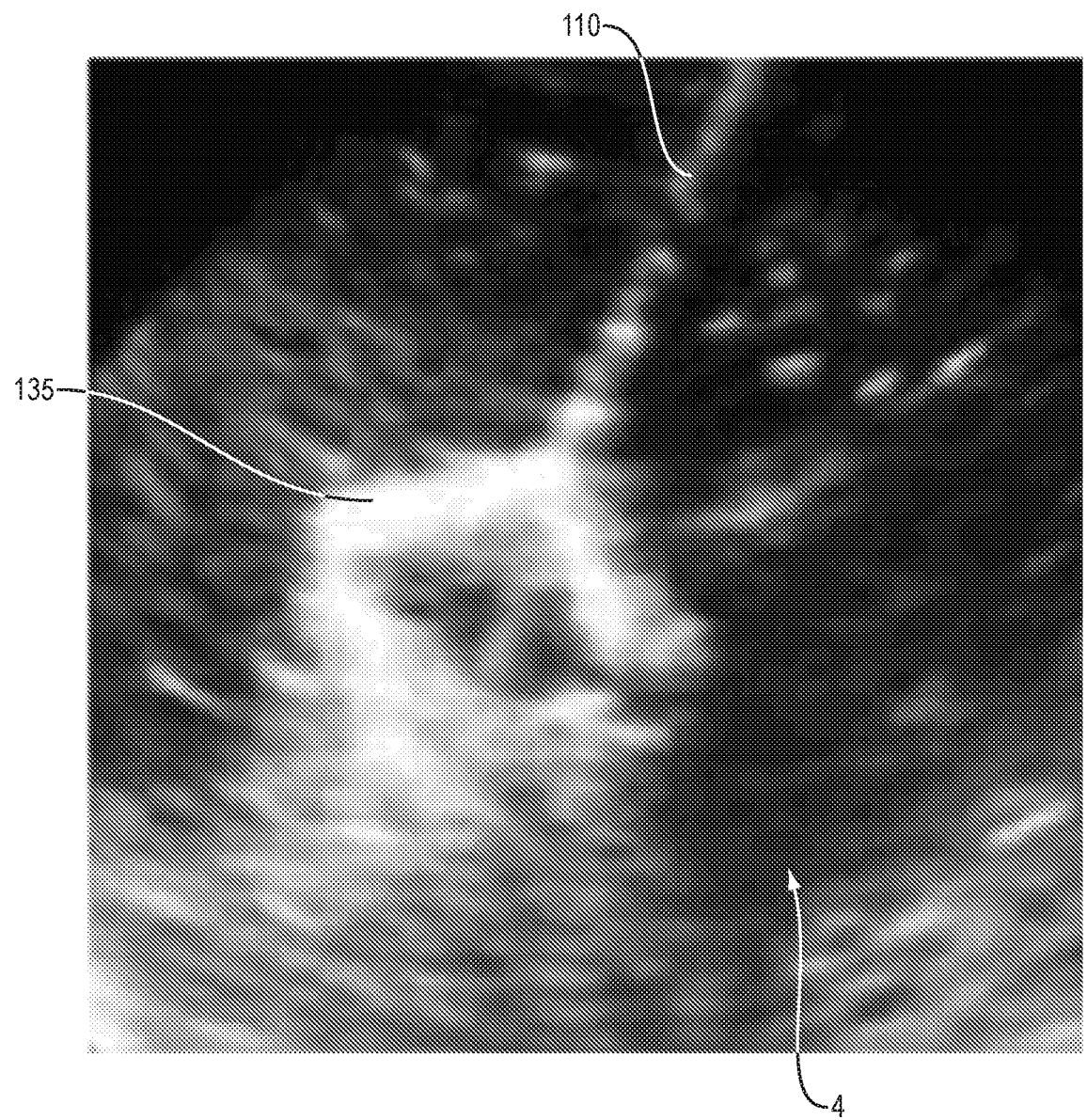

In one embodiment, a delivery system 100 of the present disclosure may be delivered (e.g., slidably disposed within) through the working channel of an endoscope. Referring to FIG. 5A, in use and by way of example, an endoscope 140 may be advanced through the esophagus into a first luminal body 2 (e.g., the stomach). The distal end 142 of the endoscope 140 may include a camera 147, light source 148 and ultrasound transducer 149. In various embodiments, the endoscope may be a conventional endoscopic ultrasound endoscope (EUS), including configurations with a bending arm ultrasound transducer that may flexed or torqued to place the ultrasound transducer into flush contact with the wall of a first luminal body. Using the endoscopic viewing mode (e.g., the light source 148 and camera 147), the distal end 142 of the endoscope 140 may be positioned adjacent to a wall portion of the first luminal body 2 which is adjacent to a previously identified (or suspected) second body 4 (e.g., pseudocyst). The second body 4 may then be imaged through the wall of the first luminal body 2 by switching to an ultrasound viewing mode (e.g., activating the ultrasound transducer 149). With the first and second locks of the handle engaged, the delivery system 100 may then be advanced through a working channel 146 of the endoscope 140. Alternatively, the delivery system 100 may be disposed within the working channel 146 of the endoscope 140 as the endoscope is advanced into the first luminal body 2. Referring to FIG. 5B, with the first and second locks still engaged, the delivery system 100 may be distally advanced under ultrasound guidance such that tissue cutting surface 126 penetrates the wall of the first luminal body 2 and extends into the second body 4. Referring to FIG. 5C, the second lock (but not the first lock) of the handle may be disengaged and the catheter 110 proximally retracted along/over the inner catheter 120 such that the distal portion 134 of the stent exits (e.g., is unconstrained from) the lumen 116 of the catheter 110 to form the distal retention member 135 within the second body 4. As depicted in FIG. 5D, the catheter 110 and distal retention member 135 may appear on an ultrasound image within the second body 4.

Figure 5E:
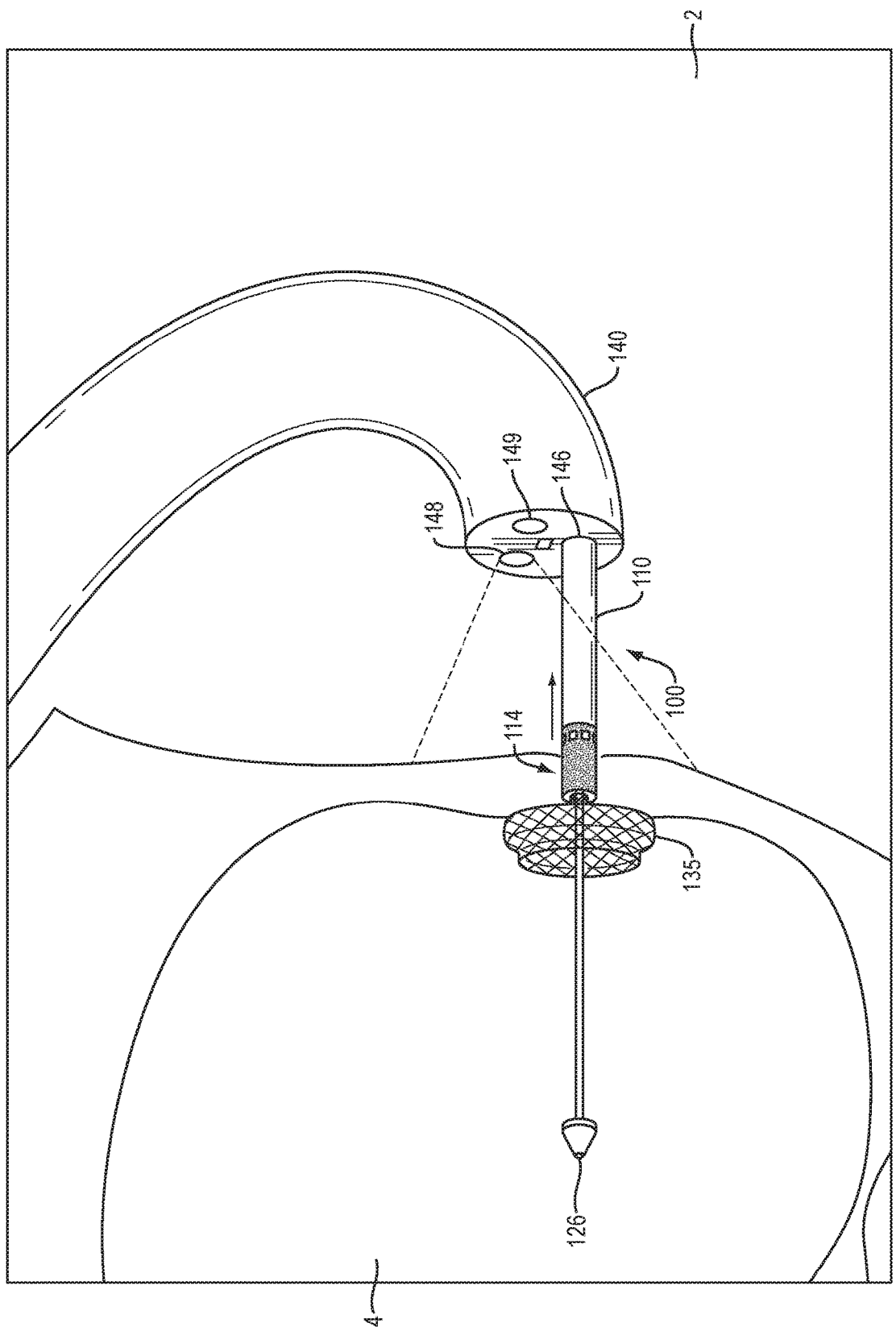
Figure 5F:
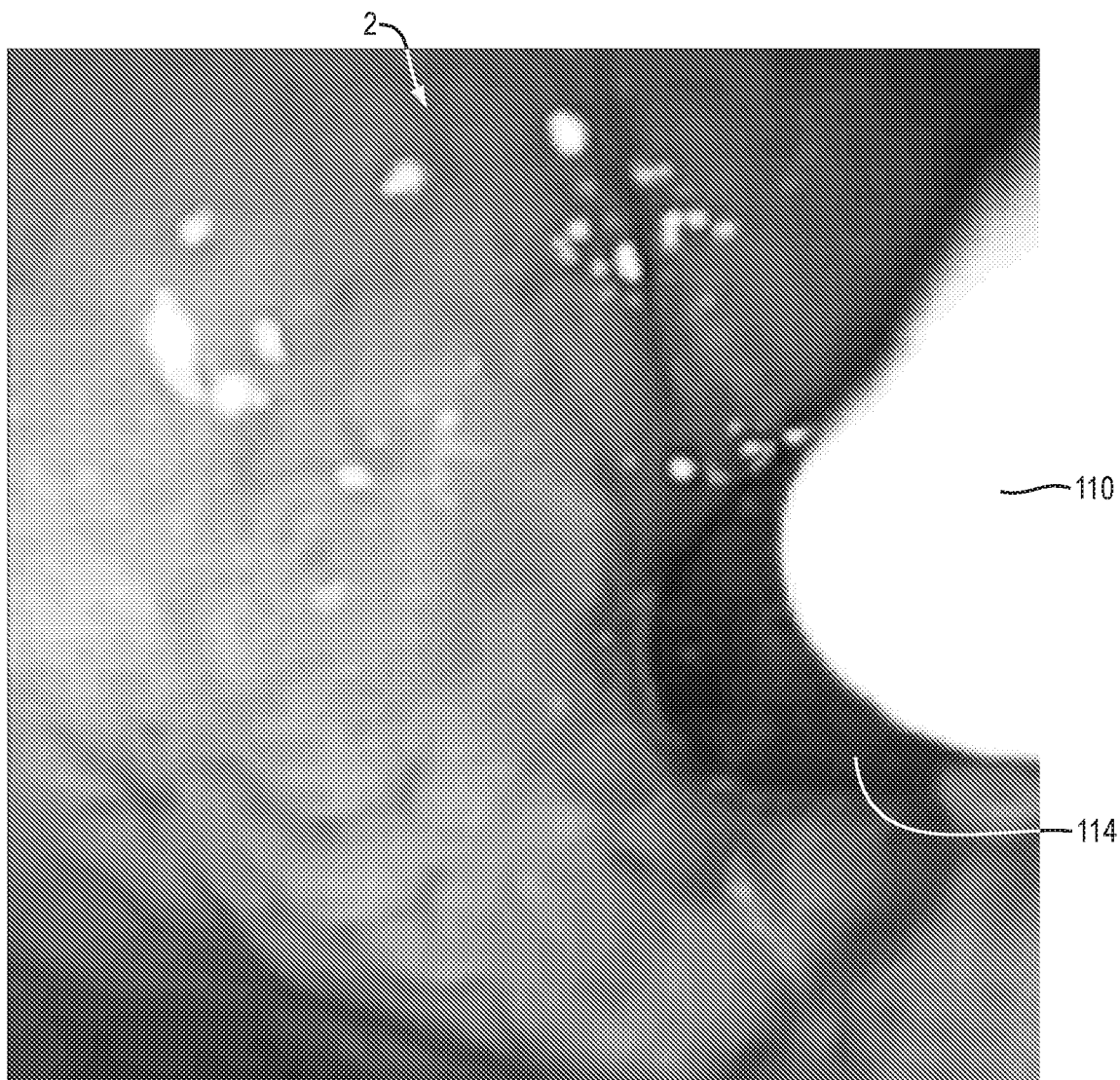

Referring to FIG. 5E, the second lock may be re-engaged and the delivery system 100 (e.g., catheter 110, inner catheter 120 and partially deployed stent) proximally retracted through the endoscope working channel 146 to place the distal retention member 135 against an inner wall of the second body 4. With the first and second locks still engaged, the endoscope 140 may be switched to the endoscopic viewing mode to allow the catheter 110 and wall of the first luminal body 2 to be visualized by the camera 147. The delivery system 100 may be further retracted until at least a portion of the primary colored marker of the distal portion 114 is visible within the first luminal body 2 (FIG. 5F). As the distal portion 114 of the catheter 110 moves from the second body 4 into the first luminal body 2, the light source 148 may illuminate one or more of the secondary marker(s) 118 (e.g., light sensors). The illuminated secondary marker (s), once they are in the first luminal body, may sense the light from the light source and may then transmit a signal to an external receiver (not shown) which emits a signal indicating that the catheter 110 is properly positioned within the first luminal body 2 for deployment of the proximal retention member 133. For example, the external receiver may emit a signal which automatically disengages the second lock (but not the first lock). Alternatively, the external receiver may emit a signal which indicates that the second lock may be safely disengaged by a separate mechanism. Referring to FIG. 5G, with the second lock disengaged, the catheter 110 may be further proximally retracted along/over the inner catheter 120 to deploy the proximal retention member 133 of the stent within the first luminal body 2. Referring to FIG. 5H, the second lock may be re-engaged and the delivery system 100 (e.g., catheter 110, inner catheter 120) proximally retracted through the deployed stent and into the working channel 146 of the endoscope 140 for removal from the body (FIG. 5H). Alternatively, the first lock may be disengaged and the inner catheter proximally retracted through the deployed stent into the catheter. The first and second locks may both be engaged, and the delivery system proximally retracted into the working channel of the endoscope for removal form the patient, as above. In various embodiments, the steps outlined in FIGS. 5A-5H may be performed out of sequence, including different sequences and/or with additional steps combined or further subdivided.

In certain medical procedures, a flow of highly cloudy and/or opaque fluids (e.g., bile, blood, pus, etc.) from the second body 2 through the lumen 136 of the partially deployed stent may occlude the light source and/or camera, thereby preventing or impairing visualization of the distal portion 114 of the catheter 110 and/or illumination of the secondary marker(s) within the first luminal body 2. In one embodiment, the delivery system 100 may include a secondary marker which includes the echogenic marker depicted in FIG. 4, rather than or in addition to the light sensors of FIGS. 1-3. In the event that the colored region of the distal portion 114 of the catheter 110 cannot be reliably visualized using the endoscopic viewing mode, or as an additional safeguard, the endoscope may be used in the ultrasound viewing mode to visualize the echogenic marker within the first luminal body 2 through cloudy/opaque fluids. The proximal retention member may then be deployed when the echogenic marker is no longer visible within the second luminal body 4, or is visualized within the first luminal body 2, as discussed above. In another embodiment, the distal portion 114 of the catheter 110 may include both echogenic and light sensor secondary markers. The endoscope may switch between the endoscopic and ultrasound viewing modes as necessary to determine when the catheter is properly positioned for deployment of the second retention member. Alternatively, the endoscopic and ultrasound viewing modes may be used simultaneously to provide alternative direct vision and imaging views of the position of the catheter within the first luminal body.

Figure 6A:
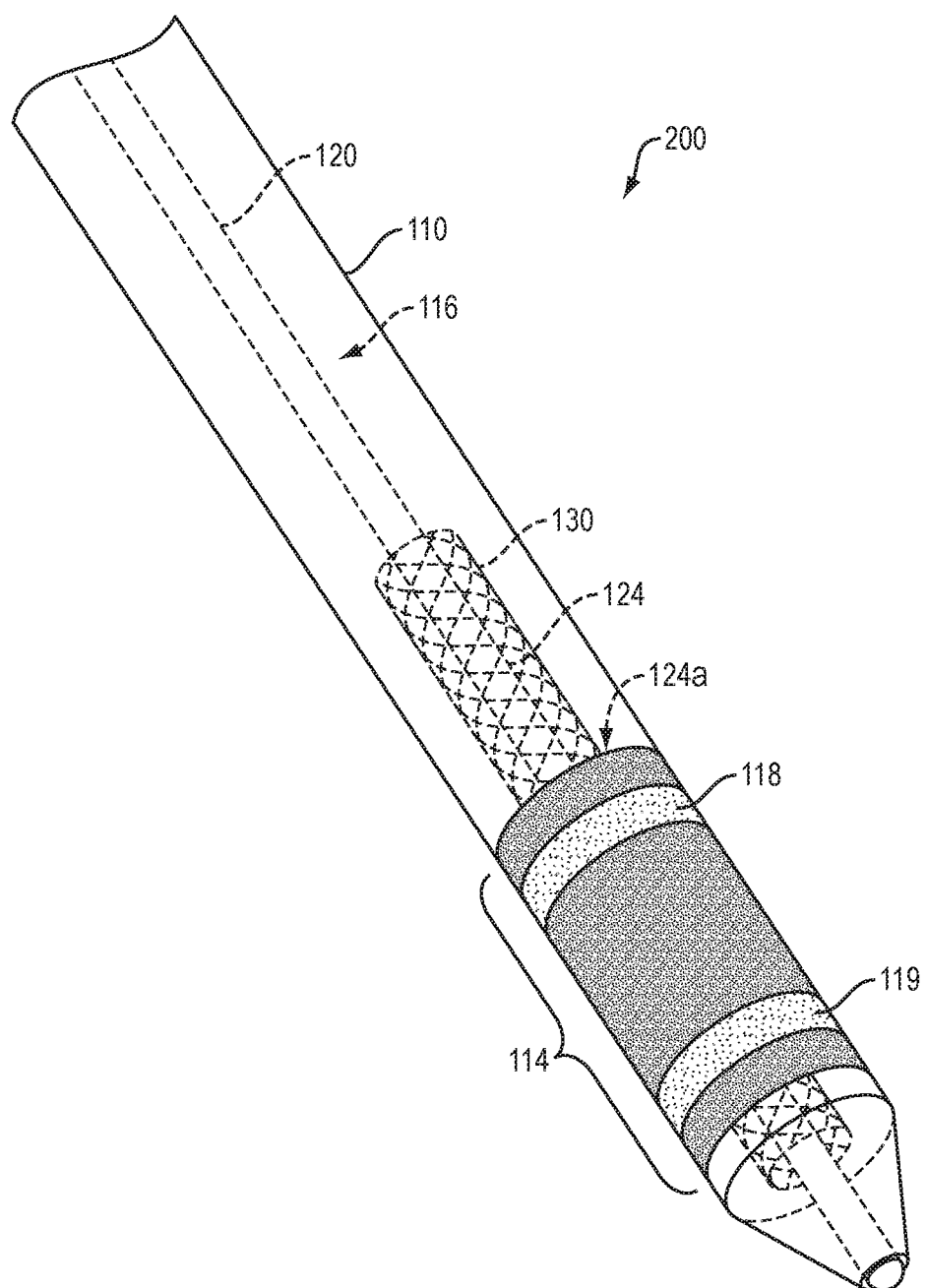

Referring to FIG. 6A, in one embodiment, the present disclosure provides a delivery system 200 comprising a catheter 110 that includes a proximal end (not shown), a distal end 112 and a lumen 116 extending therebetween. A distal portion 114 of the catheter 110 may include a primary marker, e.g., a colored region, that is different than the color of the remaining portion of the catheter. By way of non-limiting example, the distal portion 114 of the catheter 110 may include a dark color (e.g., black, etc.) and the remaining portion of the catheter may include a light color (e.g., white, etc.) which contrasts with the dark color when illuminated by a light source. The primary marker may extend a variety of distances along the distal portion 114 of the catheter (e.g., approximately 10 mm or more; approximately 20 mm or more; approximately 30 mm or more) depending on the anatomical location and/or body wall thickness of the target body lumen(s). The catheter 110 may further include secondary markers 118, 119 disposed on or within the distal portion 114 of the catheter 110. For example, secondary markers 118, 119 may include an echogenic (e.g., hyperechoic) material disposed in one or more bands about a circumference of the distal portion 114 of the catheter 110. The echogenic material may include a variety of reflective material (e.g., metals, metallic powders, etc.) and/or patterns (e.g., etching, dimples, cross-hatching, etc.) which reflect or "echo" ultrasound waves emitted from an ultrasound transducer, as are known in the art.

Still referring to FIG. 6A, the delivery system 200 may further include an inner catheter 120 slidably disposed within the lumen 116 of the catheter 110. A medical device 130 may be disposed over a distal portion 124 of the inner catheter 120 within the lumen 116. In one embodiment, the medical device 130 is a stent configured to move between a first (e.g., collapsed) configuration when disposed (e.g., constrained) within the lumen 116 of the catheter 110 and a second (e.g., expanded) configuration when not disposed with the lumen 116. The secondary marker 118 may be disposed on or within a portion of the distal portion 114 which corresponds to an approximate midpoint (e.g., saddle region) of the medical device 130, and the secondary marker 119 may be disposed on or within another portion of the distal portion 114 which corresponds to an approximate distal end (e.g., distal retention member) of the medical device 130 disposed within the lumen 116. The distal end 112 of the inner catheter 120 may further include a tissue cutting surface 126 (e.g., sharpened surface, electrocautery surface, etc.) for penetrating the wall(s) of the first luminal body and second body.

Figure 6B:
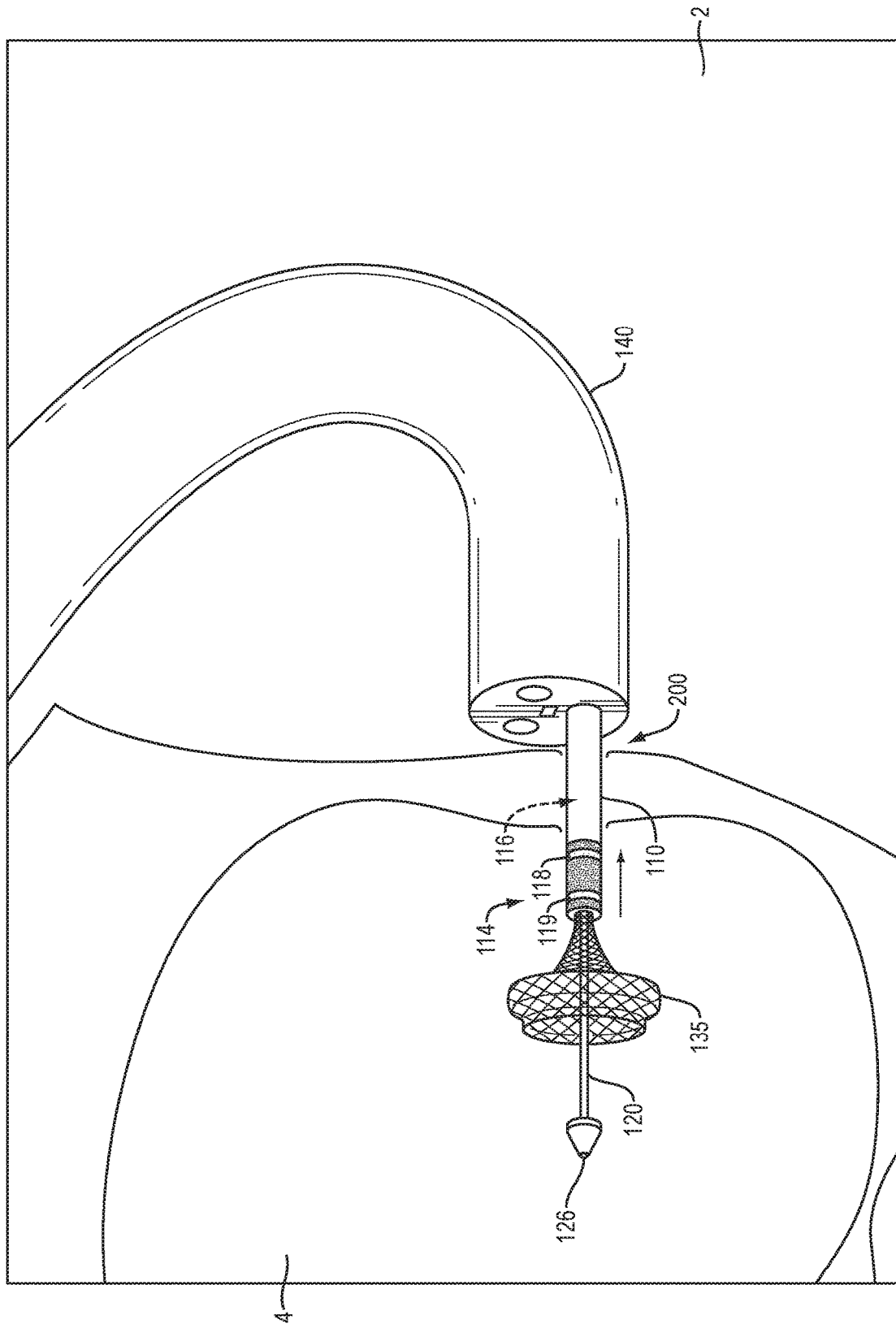

The delivery system 200 may be distally advanced under ultrasound guidance such that the tissue cutting surface 126 penetrates a first luminal body and extends into a second body 4, as discussed above. Referring to FIG. 6B, when secondary markers 118, 119 are both within the second body 4, as confirmed in the ultrasound viewing mode, the second lock (but not the first lock) of the handle may be disengaged and the catheter 110 proximally retracted along/over the inner catheter 120 such that the distal portion 134 of the stent exits (e.g., is unconstrained by) the lumen 116 of the catheter 110 to form a distal retention member 135 within the second body 4.

Figure 6C:
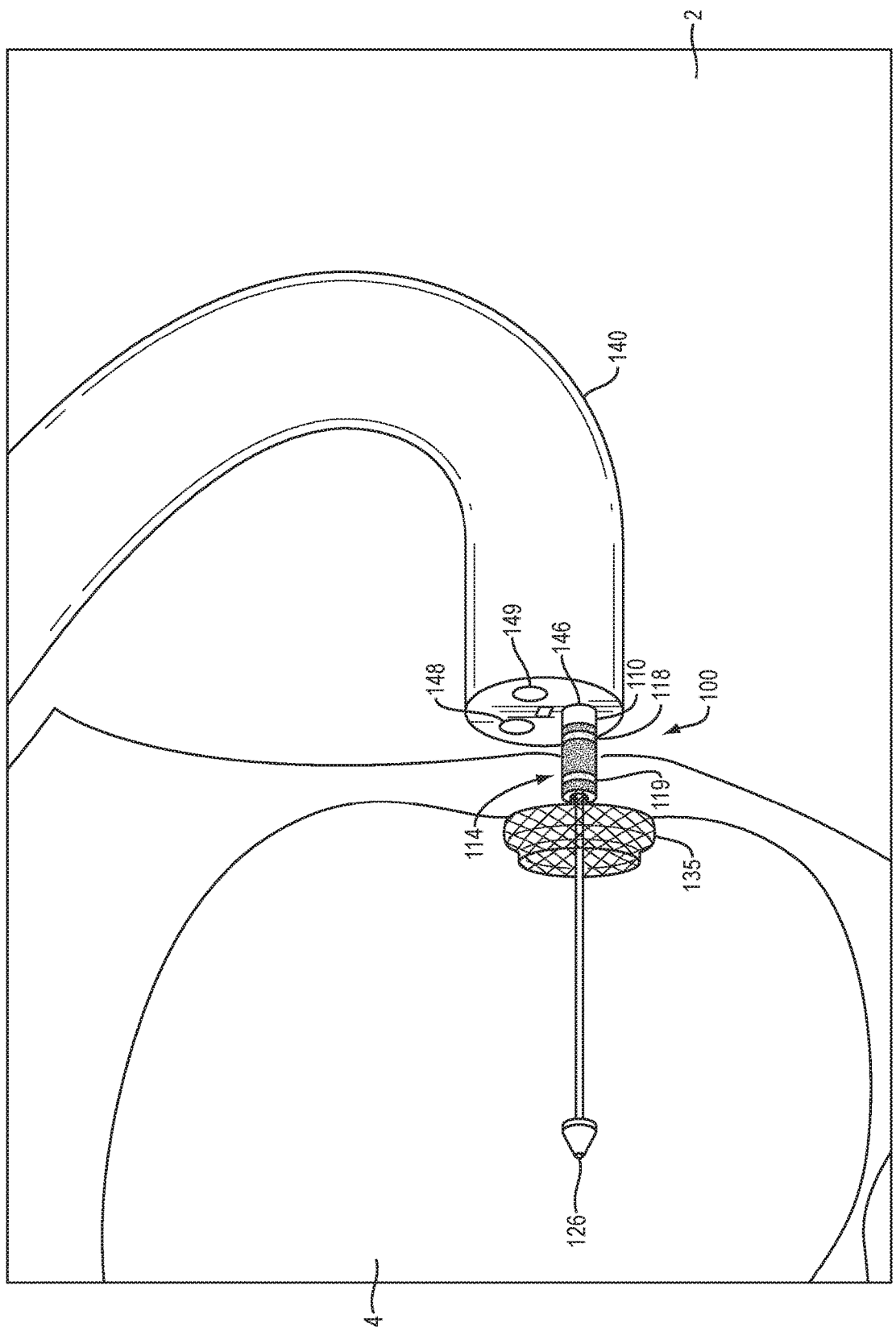

Referring to FIG. 6C, the second lock may be re-engaged and the delivery system 200 (e.g., catheter 110, inner catheter 120 and partially deployed stent) proximally retracted through the endoscope working channel 146 to place the distal retention member 135 against an inner wall of the second body 4. The delivery system 200 may be further retracted until secondary markers 118, 119 are no longer visible within the second body 4 in the ultrasound viewing mode. In addition, or alternatively, the endoscope may be switched to the endoscopic viewing mode to visualize at least a portion of the colored region of the distal portion 114 within the first luminal body 2. Referring to FIG. 6D, the second lock may be disengaged and the catheter 110 further proximally retracted along/over the inner catheter 120 to deploy a proximal retention member 133 of the stent within the first luminal body 2. The second lock may then be re-engaged and the delivery system 100 (e.g., catheter 110, inner catheter 120) proximally retracted through the deployed stent and into the working channel 146 of the endoscope 140 for removal from the body, as discussed above. In various embodiments, the steps outlined in FIGS.

6B-6D may be performed out of sequence, including different sequences and/or with additional steps combined or further subdivided.

The medical devices of the present disclosure are not limited to endoscopes, and may include a variety of systems and/or medical devices for accessing body passageways, including, for example, catheters, bronchoscopes, ureteroscopes, duodenoscopes, colonoscopes, arthroscopes, cystoscopes, hysteroscopes, and the like. Any of these systems may include or work within an ultrasound transducer, and one or more working channels which exit a front or side portion of the system or scope or extend along an outer surface thereof. In addition, systems and methods of the present disclosure may be used in a variety of medical procedures which require visual, fluoroscopy and/or ultrasound visualization. Finally, although the embodiments of the present disclosure have been described in use with an endoscope, the delivery system of the present disclosure may be positioned within the patient in the absence of an accompanying medical device.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A stent delivery system, comprising:
    a catheter comprising a primary marker and at least one secondary marker, wherein the at least one secondary marker is disposed within the primary marker;
    an inner catheter slidably disposed within a lumen of the catheter, wherein the catheter can be retracted relative to the inner catheter such that a portion of the inner catheter extends from a distal end of the catheter; and
    a stent disposed over the portion of the inner catheter, wherein the stent is constrained to a collapsed configuration when the inner catheter is disposed in the lumen of the catheter and expands to an expanded configuration when the portion of the inner catheter extends from the distal end of the catheter, wherein the stent comprises a distal retention member and a proximal retention member when in the expanded configuration, and
    wherein the secondary marker is positioned with respect to the primary marker such that confirmation within the body lumen of the secondary marker denotes that the entire proximal retention member is deployable proximally relative to a reference position.

2. The stent delivery system of claim 1, further comprising a handle coupled to the catheter and the inner catheter, the handle comprising a first lock and a second lock, which when engaged secures the outer catheter to the inner catheter.

3. The stent delivery system of claim 2, wherein the first lock, when disengaged allows the catheter to retract with respect to the inner catheter such that the distal retention member expands from the collapsed configuration.

4. The stent delivery system of claim 3, wherein the second lock, when disengaged allows the catheter to retract with respect to the inner catheter such that the proximal retention member expands from the collapsed configuration.

5. The stent delivery system of claim 1, wherein the primary marker is disposed on a distal end of the catheter.

6. The stent delivery system of claim 1, wherein the at least one secondary marker comprises a plurality of secondary markers radially disposed around a circumference of the catheter.

7. The stent delivery system of claim 1, wherein the primary marker is a darker color than the catheter.

8. The stent delivery system of claim 1, wherein the primary marker is between 10 millimeters (mm) and 30 mm in length.

9. The stent delivery system of claim 1, wherein the at least one secondary marker is disposed on a proximal portion of the primary marker.

10. A medical device system, comprising:
    a catheter comprising a primary marker and at least one secondary marker, wherein the at least one secondary marker is disposed within the primary marker;
    an inner catheter slidably disposed within a lumen of the catheter, wherein the catheter can be retracted relative to the inner catheter such that a portion of the inner catheter extends from a distal end of the catheter; and
    a medical device disposed over the portion of the inner catheter, wherein the medical device is constrained to a collapsed configuration when the inner catheter is disposed in the lumen of the catheter and expands to an expanded configuration when the portion of the inner catheter extends from the distal end of the catheter, wherein the medical device comprises a distal retention member and a proximal retention member when in the expanded configuration, and
    wherein the secondary marker is positioned with respect to the primary marker such that confirmation within the body lumen of the secondary marker denotes that the entire proximal retention member is deployable proximally relative to a reference position.

11. The medical device system of claim 10, further comprising a handle coupled to the catheter and the inner catheter, the handle comprising a first lock and a second lock, which when engaged secures the outer catheter to the inner catheter.

12. The medical device system of claim 11, wherein the first lock, when disengaged allows the catheter to retract with respect to the inner catheter such that the distal retention member expands from the collapsed configuration.

13. The medical device system of claim 12, wherein the second lock, when disengaged allows the catheter to retract with respect to the inner catheter such that the proximal retention member expands from the collapsed configuration.

14. The medical device system of claim 10, wherein the primary marker is disposed on a distal end of the catheter.

15. The medical device system of claim 10, wherein the at least one secondary marker comprises a plurality of secondary markers radially disposed around a circumference of the catheter.

16. The medical device system of claim 10, wherein the at least one secondary marker is disposed on a proximal portion of the primary marker.

17. The medical device system of claim 10, wherein the medical device is a self-expanding stent.

18. A system comprising:
    a catheter comprising a primary marker and at least one secondary marker, wherein the at least one secondary marker is disposed over the a proximal portion of the primary marker;
    an inner catheter slidably disposed within a lumen of the catheter, wherein the catheter can be retracted relative to the inner catheter such that a portion of the inner catheter extends from a distal end of the catheter; and a stent disposed over the portion of the inner catheter, wherein the stent is constrained to a collapsed configuration when the inner catheter is disposed in the lumen of the catheter and expands to an expanded configuration when the portion of the inner catheter extends from the distal end of the catheter, wherein the stent comprises a distal retention member and a proximal retention member when in the expanded configuration, and wherein the secondary marker is positioned with respect to the primary marker such that confirmation within the body lumen of the secondary marker denotes that the entire proximal retention member is deployable proximally relative to a reference position.

19. The system of claim 18, wherein the at least one secondary marker comprises a plurality of secondary markers radially disposed around a circumference of the catheter.

20. The system of claim 18, wherein the primary marker is a darker color than the catheter.

\* \* \* \* \*